US008148554B2

(12) United States Patent
Seletsky et al.

(10) Patent No.: US 8,148,554 B2
(45) Date of Patent: Apr. 3, 2012

(54) METHODS AND COMPOSITIONS FOR USE IN TREATING CANCER

(75) Inventors: Boris M. Seletsky, Andover, MA (US);
Melvin J. Yu, Andover, MA (US);
Wanjun Zheng, Londonderry, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/855,412

(22) Filed: Aug. 12, 2010

(65) Prior Publication Data

US 2011/0172446 A1    Jul. 14, 2011

Related U.S. Application Data

(63) Continuation of application No. 12/653,461, filed on Dec. 15, 2009, now abandoned, which is a continuation of application No. 12/341,154, filed on Dec. 22, 2008, now abandoned, which is a continuation of application No. 10/687,526, filed on Oct. 16, 2003, now Pat. No. 7,470,720, which is a continuation of application No. 10/272,167, filed on Oct. 16, 2002, now Pat. No. 6,653,341, which is a continuation-in-part of application No. 09/843,617, filed on Apr. 26, 2001, now Pat. No. 6,469,182, which is a continuation of application No. 09/677,485, filed on Oct. 2, 2000, now Pat. No. 6,365,759, which is a continuation of application No. 09/334,488, filed on Jun. 16, 1999, now Pat. No. 6,214,865.

(60) Provisional application No. 60/089,682, filed on Jun. 17, 1998.

(51) Int. Cl.
*C07D 407/00* (2006.01)
*C07D 323/00* (2006.01)
(52) U.S. Cl. ......... 549/414; 549/450; 549/396; 549/348
(58) Field of Classification Search .................. 549/414, 549/450, 396, 348
See application file for complete search history.

(56) References Cited

U.S. PATENT DOCUMENTS

| | | | |
|---|---|---|---|
| 5,338,865 A | 8/1994 | Kishi et al. | |
| 5,436,238 A | 7/1995 | Kishi et al. | |
| 6,214,865 B1 * | 4/2001 | Littlefield et al. | 514/450 |
| 6,365,759 B1 * | 4/2002 | Littlefield et al. | 549/414 |
| 6,469,182 B1 * | 10/2002 | Littlefield et al. | 549/214 |
| 6,653,341 B1 * | 11/2003 | Littlefield et al. | 514/450 |
| 7,470,720 B2 * | 12/2008 | Littlefield et al. | 514/450 |
| 7,982,060 B2 | 7/2011 | Austad et al. | |
| 2007/0244187 A1 | 10/2007 | Austad et al. | |
| 2009/0198074 A1 | 8/2009 | Chase et al. | |
| 2009/0203771 A1 | 8/2009 | Inanaga et al. | |
| 2011/0054194 A1 | 3/2011 | Hu | |
| 2011/0184190 A1 | 7/2011 | Endo et al. | |

FOREIGN PATENT DOCUMENTS

| | | |
|---|---|---|
| EP | 0572109 | 12/1993 |
| WO | WO 93/17690 | 9/1993 |
| WO | WO 99/65894 | 12/1999 |
| WO | WO 2005/118565 | 12/2005 |
| WO | WO 2009/046308 | 4/2009 |
| WO | WO 2009/064029 | 5/2009 |
| WO | WO 2009/124237 | 10/2009 |
| WO | WO 2011/094339 | 8/2011 |

OTHER PUBLICATIONS

Aicher et al., "Total Synthesis of Halichondrin B and Norhalichondrin B," *J. Am. Chem. Soc.* 114(8): 3162-3164 (1992).
Aicher, T.D., et al., "Synthetic Studies Towards Halichondrins: Synthesis of the C.27-C.38 Segment," *Tetrahedron Lett.* 33(12): 1549-1552 (1992).
Alley et al. "Comparison of the Relative Efficacies and Toxicities of Halichondrin B Analogues" *Proceedings of the AACR-NCI-EORTC Conference on Molecular Targets and Cancer Therapeutics*, Nov. 14-18, 2005, C230, p. 257.
Anderson, "Developing Processes for Crystallization-Induced Asymmetric Transformation," *Org. Process. Res. Dev.* 9: 800-813 (2005).
Bai et al., "Halichondrin B and Homohalichondrin B, Marine Natural Products Binding in the Vinca Domain of Tubulin. Discovery of Tubulin-based Mechanism of Action by Analysis of Differential Cytotoxicity Data," *J. Biol. Chem.* 266(24): 15882-15889 (1991).
Bernet et al., "Carbocyclische Verbindungen aus Monosacchariden. Umsetzungen in der Glucosereihe," *Helv. Chim. Acta.* 62: 1990-2016 (1979).
Blanchette et al., "Horner-Wadsworth-Emmons Reaction: Use of Lithium Chloride and an Amine for Base-Sensitive Compounds," *Tetrahedron Lett.* 25(21): 2183-2186 (1984).
Burke, S.D., et al., "Enantioselective Synthesis of a Halichondrin B C(20)→ C(36) Precursor," *Tetrahedron Lett.*, 36(39): 7023-7026 (1995).
Burke, S.D., et al., "Synthesis of a C(22)—C(34) Halichondrin B Precursor via Ring Opening—Double Ring Closing Metathesis," *J. Org. Chem.*, 63: 8626-8627 (1998).
Burke, S.D., et al., "Synthesis of a C(22)→ C(34) Halichondrin Precursor via a Double Dioxanone-to-Dihydropyran Rearrangement," *Tetrahedron Lett.*, 32(32): 3961-3964 (1991).
Burke, S.D., et al., "Synthetic Studies Toward Complex Polyether Macrolides of Marine Origin," *Spec. Publ. R. Soc. Chem.*, 198: (Anti-Infectives), 73-85 (1997).
Chen C., et al., "Ni(II)/Cr(II)-Mediated Coupling Reaction: An Asymmetric Process," *J. Org. Chem.*, 60: 5386-5387 (1995).
Choi et al., "Assymmetric Ni(II)/Cr(II)-Mediated Coupling Reaction: Catalytic Process," *Org. Lett.* 4(25): 4435-4438 (2002).
Choi et al., "Synthetic Studies on the Marine Natural Product Halichondrins," *Pure Appl. Chem.* 75(1): 1-17 (2003).
Cooper, A.J., et al., "Total Synthesis of Halichondrin B from Common Sugars: An F-Ring Intermediate from D-Glucose and Efficient Construction of the C1 to C21 Segment," *Tetrahedron Lett.*, 34(51): 8193-8196 (1993).

(Continued)

*Primary Examiner* — Andrew D Kosar
*Assistant Examiner* — Raymond Covington
(74) *Attorney, Agent, or Firm* — Clark & Elbing LLP

(57) ABSTRACT

The invention provides methods and compositions for use in treating diseases associated with excessive cellular proliferation, such as cancer, and intermediates for the synthesis of such compositions.

7 Claims, No Drawings

OTHER PUBLICATIONS

Dabybeen et al. "Comparison of the Activities of the Truncated Halichondrin B Analog NSC 707389 (E7389) with Those of the Parent Compound and a Proposed Binding Site on Tubulin" *Molecular Pharmacology* 2006, 70:1866.

Dong, C. et al. "New Syntheses of E7389 C14-C35 and Halichondrin C14-C38 Building Blocks: Reductive Cyclization and Oxy-Michael Cyclization Approaches" *J. Am. Chem. Soc.* 131:15642-15646 (2009).

Duan and Kishi, "Synthetic studies on halichondrins: A new practical synthesis of the C.1-C.12 segment," *Tetrahedron Lett.* 34(47):7541-7544 (1993).

Flemming et al., "Nitrile Anion Cyclizations," *Tetrahedron* 58:1-23 (2002).

Hirata et al., "Halichondrins—Antitumor Polyether Macrolides from a Marine Sponge," *Pure Appl. Chem.* 58(5): 701-710 (1986).

Hori et al., "Efficient Synthesis of 2,3- *trans*-Tetrahydropyrans and Oxepanes: Rearrangement-Ring Expansion of Cyclic Ethers Having a Chloromethanesulfonate," *Tetrahedron Lett.* 40: 2145-2148 (1999).

Horita et al., "Synthetic Studies of Halichondrin B, an Antitumor Polyether Macrolide Isolated from a Marine Sponge. 8. Synthesis of the Lactone Part (C1-C36) via Horner-Emmons Coupling Between C1-C15 and C16-C36 Fragments and Yamaguchi Lactonization," *Tetrahedron Lett.* 38(52): 8965-8968 (1997).

Horita, K., et al., "Research on Anti-Tumor Active Site of Marine Source Natural Product, Halichondrin B.," *International Congress Series*, 1157 (Towards Natural Medicine Research in the $21^{st}$ Century), 327-336 (1998).

Horita, K., et al., "Synthetic Studies of Halichondrin B, an Antitumor Polyether Macrolide Isolated From a Marine Sponge. 2. Efficient Synthesis of C16-C26 Fragments via Construction of the D Ring by a Highly Stereocontrolled Iodoetherification," *Synlett*, 40-43 (1994).

Horita, K., et al., "Synthetic Studies of Halichondrin B, an Antitumor Polyether Macrolide Isolated from a Marine Sponge. 3. Synthesis of C27-C36 Subunit via Completely Stereoselective C-Glycosylation to the F ring," *Synlett*, 43-45 (1994).

Horita, K., et al., "Synthetic Studies of Halichondrin B, an Antitumor Polyether Macrolide Isolated from a Marine Sponge. 7. Synthesis of Two C27-C36 Units via Construction of the F ring and Completely Stereoselective C-Glycosylation Using Mixed Lewis Acids," *Chem. Pharm. Bull.*, 45(10): 1558-1572 (1997).

Horita, K., et al., "Synthetic Studies on Halichondrin B, an Antitumor Polyether Macrolide Isolated from a Marine Sponge. 9. Synthesis of the C16-C36 unit via Stereoselective Construction of the D and E Rings," *Chem. Pharm. Bull.*, 46(8): 1199-1216 (1998).

Horita, K., et al., "Synthetic Study of a Highly Antitumorigenic Marine Phytochemical, Halichondrin B," *Phytochemicals and Phytopharmaceuticals*, Shahihi, F. and Ho, C.-T., Eds., AOCS Press, Champaign, IL, 2000, 386-397.

Jackson et al., "A Total Synthesis of Norhalichondrin B" *Angew. Chem. Int. Ed.* 48: 2346-2350 (2009).

Jackson et al., "The Halichondrins and E7389," *Chem. Rev.* 109: 3044-3079 (2009).

Jiang, L., et al., "A Novel Route to the F-Ring of Halichondrin B. Diastereoselection in Pd(0)-Mediated *meso* and $C_2$ Diol Desymmetrization," *Org. Lett.*, 4(20): 3411-3414 (2002).

Jiang, L., et al., "A Practical Synthesis of the F-Ring of Halichondrin B via Ozonolytic Desymmetrization of a $C_2$-Symmetric Dihydroxycyclohexene," *J. Org. Chem.*, 68: 1150-1153 (2003).

Kim, D. et al. "New Syntheses of E7389 C14-C35 and Halichondrin C14-C38 Building Blocks: Double-Inversion Approach" *J. Am. Chem. Soc.* 131: 15636-15641 (2009).

Kurosu et al. "Fe/Cr- and Co/Cr-Mediated Catalytic Asymmetric 2-Haloallylations of Aldehydes," *J. Am. Chem. Soc.* 126: 12248-12249 (2004).

Mattocks, "Novel Reactions of Some α-Acyloxy Acid Chlorides," *J. Chem. Soc.* 371: 1918-1930 (1964).

Mattocks, "Novel Reactions of Some α-Acyloxy-acid Halides," *J. Chem. Soc.* 932: 4840-4845 (1964).

Mitsunobu, "The Use of Diethyl Azodicarboxylate and Triphenylphosphine in Synthesis and Transformation of Natural Products," *Synthesis*. 1-28 (1981).

Newman, "Drug Evaluation: Eribulin, a Simplified Ketone Analog of the Tubulin Inhibitor Halichondrin B, for the Potential Treatment of Cancer," *Curr. Opin. Invest. Drugs*. 8:1057-1066 (2007).

Sakamoto et al., "Stereoselective Ring Expansion via Bicyclooxonium Ion. A Novel Approach to Oxocanes," *Org. Lett.* 4(5):675-678 (2002).

Schreiber, "Hydrogen Transfer from Tertiary Amines to Trifluoroacetic Anhydride," *Tetrahedron Lett.* 21: 1027-1030 (1980).

Seletsky et al. "Structurally simplified macrolactone analogues of halichondrin B" *Bioorg. Med. Chem. Lett.* 14:5547-5550 (2004).

Stamos et al., "A mild preparation of vinyliodides from vinylsilanes," *Tetrahedron Lett.* 37(48): 8647-8650 (1996).

Stamos et al., "New Synthetic Route to the C.14-C.38 Segment of Halichondrins," *J. Org. Chem.* 62:7552-7553 (1997).

Stamos et al., "Synthetic Studies on Halichondrins: A Practical Synthesis of the C.1-C.13 Segment," *Tetrahedron Lett.* 37(48): 8643-8646 (1996).

Stamos, D.P., et al., "Ni(II)/Cr(II)-Mediated Coupling Reaction: Beneficial Effects of 4-Tert-Butylpyridine as an Additive and Development of New and Improved Workup Procedures," *Tetrahedron Lett.*, 38(36): 6355-6358 (1997).

Tokunaga et al., "Asymmetric Catalysis with Water: Efficient Kinetic Resolution of Terminal Epoxides by Means of Catalytic Hydrolysis," *Science* 277: 936-938 (1997).

Towle et al. "Halichondrin B Macrocyclic Ketone Analog E7389: Medicinal Chemistry Repair of Lactone Ester Instability Generated During Structural Simplification to Clinical Candidate" *Annual Meeting of the American Association for Cancer Research*, Apr. 6-10, 2002, 5721.

Towle et al. "In Vitro and In Vivo Anticancer Activities of Synthetic Macrocyclic Ketone Analogues of Halichondrin B" *Cancer Research* 2001, 61:1013.

Uemura et al., "Norhalichondrin A: An Antitumor Polyether Macrolide from a Marine Sponge," *J. Am. Chem. Soc.* 107: 4796-4798 (1985).

Vahdat et al., "Phase II Study of Eribulin Mesylate, a Halichondrin B Analog, in Patients with Metastatic Breast Cancer Previously Treated with an Anthracycline and a Taxane," *J. Clin. Oncol.* 27(18): 2954-2961 (2009).

Wan et al., "Asymmetric Ni(II)/Cr(II)-Mediated Coupling Reaction: Stoichiometric Process," *Org. Lett.* 4(25): 4431-4434 (2002).

Wang et al. "Structure-Activity Relationships of Halichondrin B Analogues: Modifications at C.30-C.38" *Bioorg. Med. Chem. Lett.* 2000, 10:1029.

Xie, C., et al., "Synthesis of the C20-C26 Building Block of Halichondrins via a Regiospecific and Stereoselective $S_N 2$' Reaction," *Org. Lett.*, 4(25): 4427-4429 (2002).

Yang et al., "Second Generation Synthesis of C27-C35 Building Block of E7389, a Synthetic Halichondrin Analogue," *Org. Lett.* 11(20): 4516-4519 (2009).

Yu et al., New Synthetic Route to the C.14-C.21 Fragment of Halichondrin B, Book of Abstracts, $219^{th}$ ACS National Meeting, San Francisco, CA, Mar. 26-30, 2000 (2000).

Yu et al., *Anticancer Agents from Natural Products;* CRC Press: Boca Raton, FL, 241-265. (2005).

Zheng et al., "Macrocyclic Ketone Analogues of Halichondrin B," *Bioorg. Med. Chem. Lett.* 14: 5551-5554 (2004).

Zheng, W. et al. "Synthetic macrocyclic ketone analogs of halichondrin B: structure-activity relationships" American Association for Cancer Research, San Francisco, CA Apr. 1-5, 2000, 1915.

\* cited by examiner

METHODS AND COMPOSITIONS FOR USE IN TREATING CANCER

CROSS-REFERENCE TO RELATED APPLICATIONS

This application is a continuation of, and claims priority from, U.S. patent application Ser. No. 12/653,461, filed Dec. 15, 2009, which is a continuation of U.S. patent application Ser. No. 12/341,154, filed Dec. 22, 2008 (now abandoned), which is a continuation of U.S. patent application Ser. No. 10/687,526, filed Oct. 16, 2003 (now U.S. Pat. No. 7,470,720), which is a continuation of U.S. patent application Ser. No. 10/272,167, filed Oct. 16, 2002 (now U.S. Pat. No. 6,653,341), which is a continuation-in-part of U.S. patent application Ser. No. 09/843,617, filed Apr. 26, 2001 (now U.S. Pat. No. 6,469,182), which is a continuation of U.S. patent application Ser. No. 09/677,485, filed Oct. 2, 2000 (now U.S. Pat. No. 6,365,759), which is a continuation of U.S. patent application Ser. No. 09/334,488, filed Jun. 16, 1999 (now U.S. Pat. No. 6,214,865), which claims benefit of U.S. Provisional Patent Application No. 60/089,682, filed Jun. 17, 1998 (now lapsed). The contents of the earlier filed applications are incorporated by reference herein in their entirety.

FIELD OF THE INVENTION

This invention relates to methods and compositions for use in treating cancer and intermediates for the synthesis of such compositions.

BACKGROUND OF THE INVENTION

Cancer is a term used to describe a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine the extent of metastasis, systemic approaches to therapy are usually undertaken when any evidence of spread is detected. These approaches involve the administration of chemotherapeutic drugs that interfere with the growth of rapidly dividing cells, such as cancer cells.

Halichondrin B is a structurally complex, macrocyclic compound that was originally isolated from the marine sponge *Halichondria okadai* and subsequently was found in *Axinella* sp., *Phakellia carteri*, and *Lissondendryx* sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, beta$^S$-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

SUMMARY OF THE INVENTION

The invention features a compound having the formula:

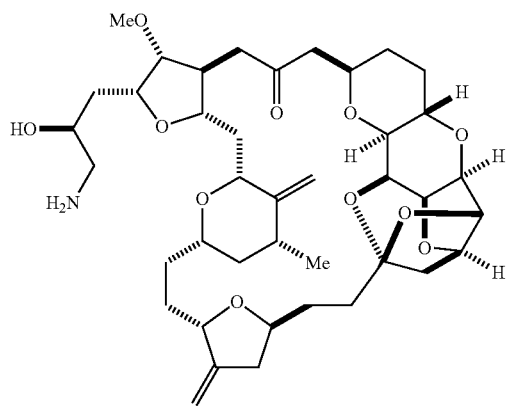

B1939 or a pharmaceutically acceptable salt thereof.

The invention further features compounds that can be employed in the synthesis of B1939, pharmaceutically acceptable salts thereof, and other halichondrin analogs described in U.S. Pat. No. 6,214,865 and methods of synthesizing B1939 or a pharmaceutically acceptable salt thereof using these compounds:

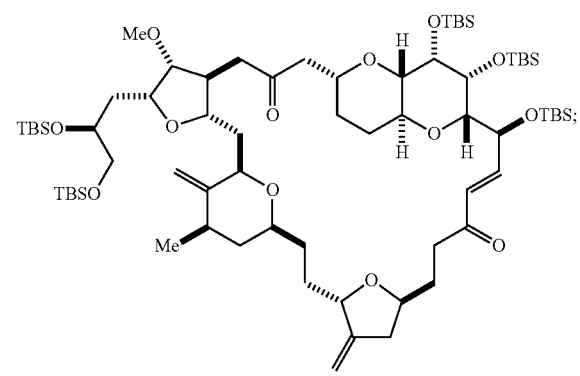

B2301

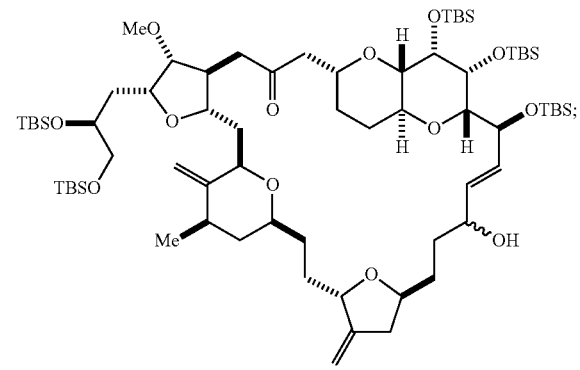

B2302/B2303

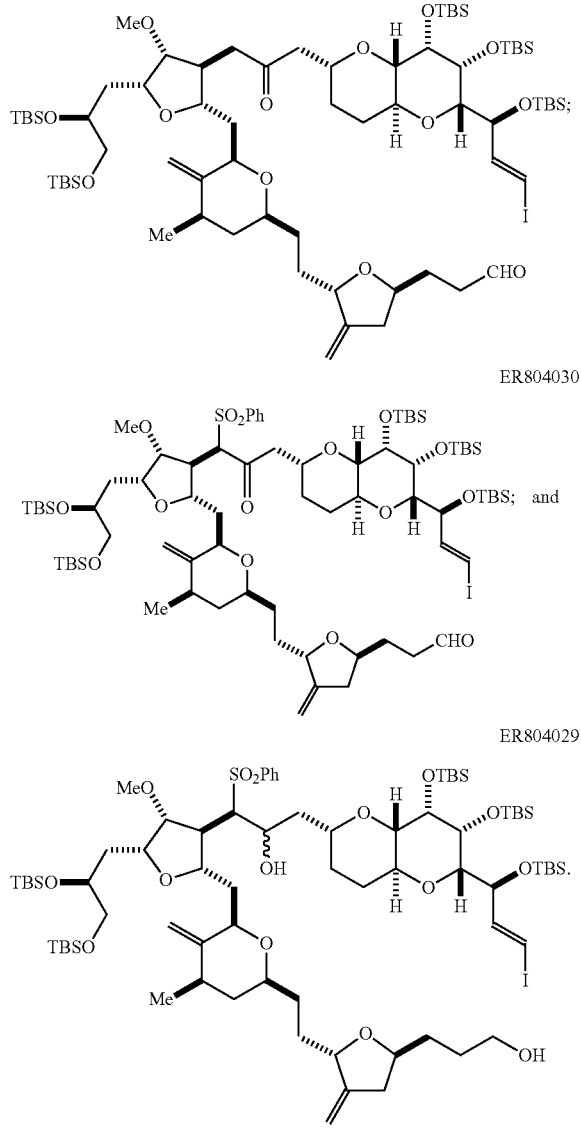

The invention provides methods of treating cancer in a patient, involving administration of a compound having the formula:

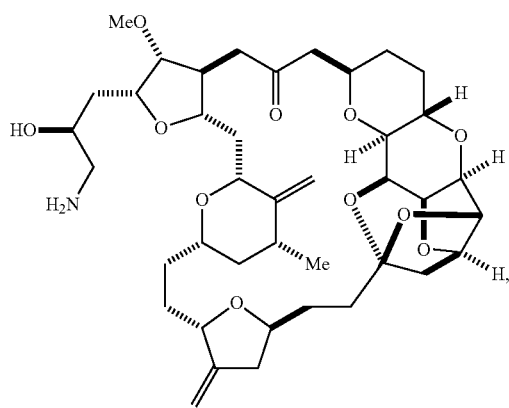

or a pharmaceutically acceptable salt thereof, which is carried out in combination with a second approach to treatment.

The second approach to treatment can involve administration of a chemotherapeutic drug to the patient. Examples of types of such drugs include antimetabolites, antibiotics, alkylating agents, plant alkaloids, and hormonal agents.

An antimetabolite, such as gemcitabine, can be used in the invention in the treatment of, for example, non-small cell lung carcinoma, pancreatic cancer, or metastatic breast cancer. An antimetabolite, such as capecitabine, can also be used in the invention in the treatment of, for example, breast cancer or colorectal cancer.

An example of a type of antibiotic that can be used in the invention is anthracyclines (e.g., doxorubicin), which can be used in the invention, for example, in the treatment of breast cancer.

Alkylating agents, such as carboplatinum or cisplatinum, can be used in the invention to treat, for example, non-small cell lung cancer or ovarian cancer.

Plant alkaloids, such as irinotecan and topotecan, can be used in the invention to treat, for example, colorectal cancer, ovarian cancer, or non-small cell lung carcinoma.

The second approach to treatment can also involve administration of an anticoagulant or antithrombotic agent (e.g., heparin) to the patient.

The invention also provides compositions that include a compound having the formula:

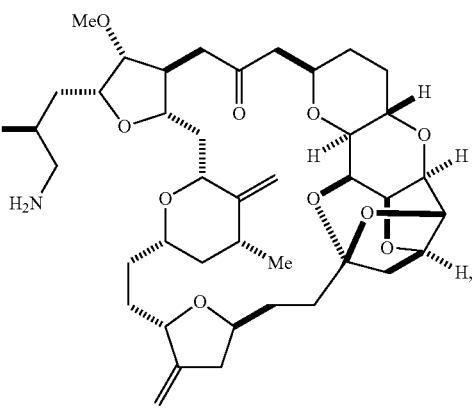

or a pharmaceutically acceptable salt thereof, in combination with a second anti-cancer drug. These drugs include, for example, any of the chemotherapeutic agents mentioned elsewhere herein, as well as others.

Other features and advantages of the invention will be apparent from the following detailed description and the claims.

DETAILED DESCRIPTION OF THE INVENTION

Compounds of general formula 4, e.g., B1939, can be prepared by the route outlined in Scheme 1.

Scheme 1

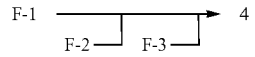

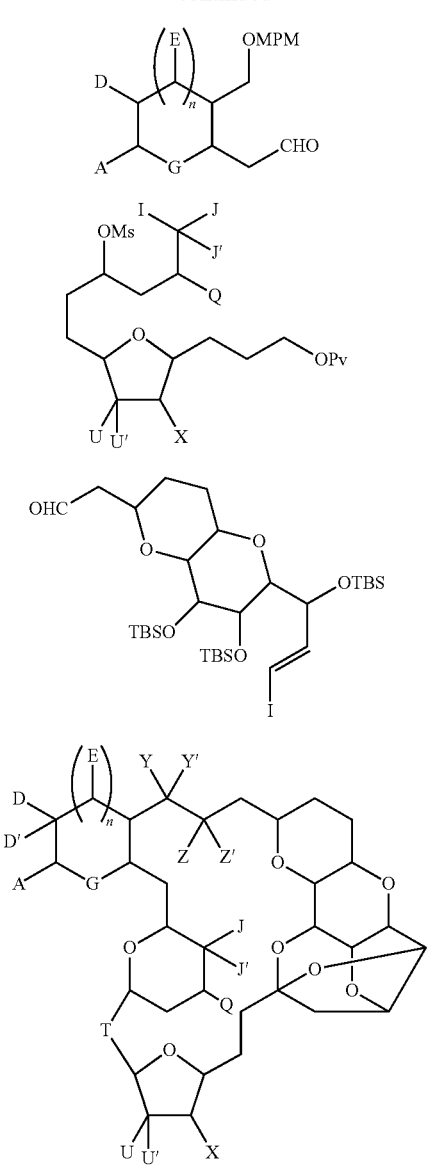

In formula (I), A is a $C_{1-6}$ saturated or $C_{2-6}$ unsaturated hydrocarbon skeleton, the skeleton being unsubstituted or having between 1 and 13 substituents, preferably between 1 and 10 substituents, e.g., at least one substituent selected from cyano, halo, azido, $Q_1$, and oxo. Each $Q_1$ is independently selected from $OR_1$, $SR_1$, $SO_2R_1$, $OSO_2R_1$, $NR_2R_1$, $NR_2(CO)R_1$, $NR_2(CO)(CO)R_1$, $NR_4(CO)NR_2R_1$, $NR_2(CO)OR_1$, $(CO)OR_1$, $O(CO)R_1$, $(CO)NR_2R_1$, and $O(CO)NR_2R_1$. The number of substituents can be, for example, between 1 and 6, 1 and 8, 2 and 5, or 1 and 4. Throughout the disclosure, numerical ranges are understood to be inclusive.

Each of $R_1$, $R_2$, $R_4$, $R_5$, and $R_6$ is independently selected from H, $C_{1-6}$ alkyl, $C_{1-6}$ haloalkyl, $C_{1-6}$ hydroxyalkyl, $C_{1-6}$ aminoalkyl, $C_{6-10}$ aryl, $C_{6-10}$ haloaryl (e.g., p-fluorophenyl or p-chlorophenyl), $C_{6-10}$ hydroxyaryl, $C_{1-4}$ alkoxy-$C_6$ aryl (e.g., p-methoxyphenyl, 3,4,5-trimethoxyphenyl, p-ethoxyphenyl, or 3,5-diethoxyphenyl), $C_{6-10}$ aryl-$C_{1-6}$ alkyl (e.g., benzyl or phenethyl), $C_{1-6}$ alkyl-$C_{6-10}$ aryl, $C_{6-10}$ haloaryl-$C_{1-6}$ alkyl, $C_{1-6}$ alkyl-$C_{6-10}$ haloaryl, ($C_{1-3}$ alkoxy-$C_6$ aryl)-$C_{1-3}$ alkyl, $C_{2-9}$ heterocyclic radical, $C_{2-9}$ heterocyclic radical-$C_{1-6}$ alkyl, $C_{2-9}$ heteroaryl, and $C_{2-9}$ heteroaryl-$C_{1-6}$ alkyl. There may be more than one $R_1$, for example, if A is substituted with two different alkoxy($OR_1$) groups such as butoxy and 2-aminoethoxy.

Examples of A include 2,3-dihydroxypropyl, 2-hydroxyethyl, 3-hydroxy-4-perfluorobutyl, 2,4,5-trihydroxypentyl, 3-amino-2-hydroxypropyl, 1,2-dihydroxyethyl, 2,3-dihydroxy-4-perfluorobutyl, 3-cyano-2-hydroxypropyl, 2-amino-1-hydroxy ethyl, 3-azido-2-hydroxypropyl, 3,3-difluoro-2,4-dihydroxybutyl, 2,4-dihydroxybutyl, 2-hydroxy-2(p-fluorophenyl)-ethyl, —$CH_2$(CO)(substituted or unsubstituted aryl), —$CH_2$(CO)(alkyl or substituted alkyl, such as haloalkyl or hydroxyalkyl), and 3,3-difluoro-2-hydroxypent-4-enyl.

Examples of $Q_1$ include —NH(CO)(CO)-(heterocyclic radical or heteroaryl), —$OSO_2$-(aryl or substituted aryl), —O(CO)NH-(aryl or substituted aryl), aminoalkyl, hydroxyalkyl, —NH(CO)(CO)-(aryl or substituted aryl), —NH(CO)(alkyl)(heteroaryl or heterocyclic radical), O(substituted or unsubstituted alkyl)(substituted or unsubstituted aryl), and —NH(CO)(alkyl)(aryl or substituted aryl).

Each of D and D' is independently selected from $R_3$ and $OR_3$, wherein $R_3$ is H, $C_{1-3}$ alkyl, or $C_{1-3}$ haloalkyl. Examples of D and D' are methoxy, methyl, ethoxy, and ethyl. In some embodiments, one of D and D' is H.

The value for n is 1 or preferably 0, thereby forming either a six-membered or five-membered ring. This ring can be unsubstituted or substituted, e.g., where E is $R_5$ or $OR_5$, and can be a heterocyclic radical or a cycloalkyl, e.g., where G is S, $CH_2$, $NR_6$, or preferably O.

Each of J and J' is independently H, $C_{1-6}$ alkoxy, or $C_{1-6}$ alkyl; or J and J' taken together are =$CH_2$ or —O-(straight or branched $C_{1-5}$ alkylene)-O—, such as exocyclic methylene or ethylene. Q is $C_{1-3}$ alkyl and is preferably methyl. T is ethylene or ethenylene, optionally substituted with $(CO)OR_7$, where $R_7$ is H or $C_{1-6}$ alkyl. Each of U and U' is independently H, $C_{1-6}$ alkoxy, or $C_{1-6}$ alkyl; or U and U' taken together are =$CH_2$ or —O-(straight or branched $C_{1-5}$ alkylene)-O—. X is H or $C_{1-6}$ alkoxy. Each of Y and Y' is independently H or $C_{1-6}$ alkoxy; or Y and Y' taken together are =O, =$CH_2$, or —O-(straight or branched $C_{1-5}$ alkylene)-O—. Each of Z and Z' is independently H or $C_{1-6}$ alkoxy; or Z and Z' taken together are =O, =$CH_2$, or —O— (straight or branched $C_{1-5}$ alkylene)-O—.

The invention features compounds of sufficient stability to be suitable for pharmaceutical development. The invention also features pharmaceutically acceptable salts of disclosed compounds, disclosed novel synthetic intermediates, pharmaceutical compositions containing one or more disclosed compounds, methods of making the disclosed compounds or intermediates, and methods of using the disclosed compounds or compositions. Methods of use include methods for reversibly or irreversibly inhibiting mitosis in a cell, and for inhibiting cancer or tumor growth in vitro, in vivo, or in a patient. The invention also features methods for identifying an anti-mitotic or anti-cancer agent, such as a reversible or, preferably, an irreversible agent.

Key fragment F-2 exemplified by vinyl iodide compound X2 can be prepared according to the procedure of Kishi, et al. (Total synthesis of halichondrin B and norhalichondrin B. Aicher, T. D.; Buszek, K. R.; Fang, F. G.; Forsyth, C. J.; Jung, S. H.; Kishi, Y.; Matelich, M. C.; Scola, P. M.; Spero, D. M.; Yoon, S. K. J. Am. Chem. Soc. 1992, 114, 3162-4).

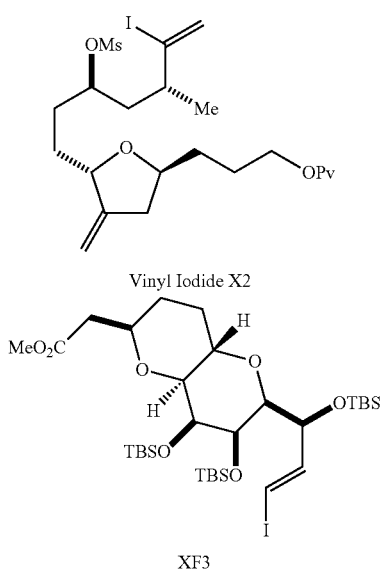

Vinyl Iodide X2

XF3

Key fragment F-3 can be obtained by DIBALH reduction of the corresponding methyl ester, XF3, prepared according to the procedure of Stamos, et al. [Synthetic studies on halichondrins: a practical synthesis of the C.1-C.13 segment. Stamos, D. P.; Kishi, Y. *Tetrahedron Lett.* 1996, 37, 8643-8646]. Key fragment F-1 can be synthesized as described in U.S. Pat. No. 6,214,865.

Using B1793 as a representative example, coupling of the three key fragments proceeded as outlined in U.S. Pat. No. 6,214,865: Nozaki-Hiyama-Kishi coupling of fragments F-1 and F-2 followed by intramolecular Williamson ether formation furnished tetrahydropyran. Protecting group modification afforded primary iodide. Halogen-metal exchange reaction and coupling with key fragment F-3 furnished a mixture of diastereomeric alcohols. Additional protecting group manipulation and oxidation followed by an intramolecular Nozaki-Hiyama-Kishi reaction afforded an intermediate, which when oxidized and treated with TBAF underwent intramolecular hetero-Michael ring closure. PPTs mediated acetal formation furnished B1793.

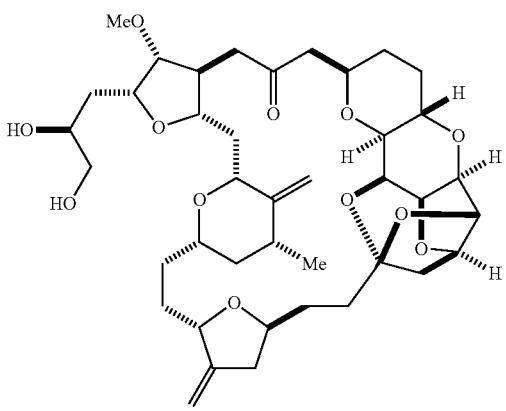

B1793

One or more hydroxyl groups could be converted to the corresponding amino groups with subsequent coupling with an activated carbonyl component. Displacement of the sulfonyl intermediate by carbon or heteroatom nucleophiles could also be readily accomplished to yield B1939.

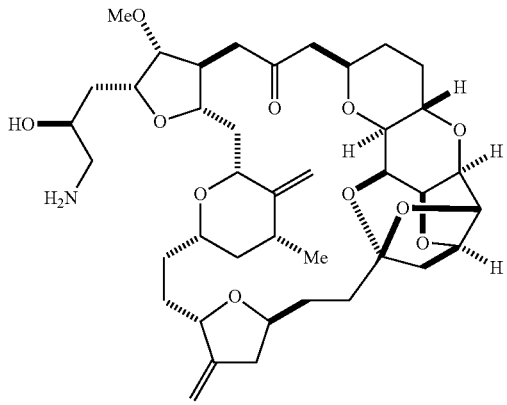

B1939

B2304 may be prepared as follows.

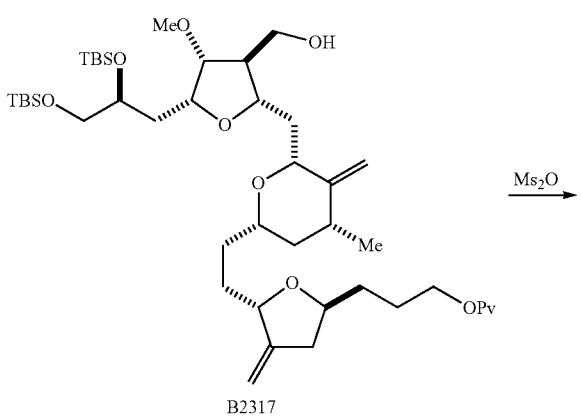

B2317

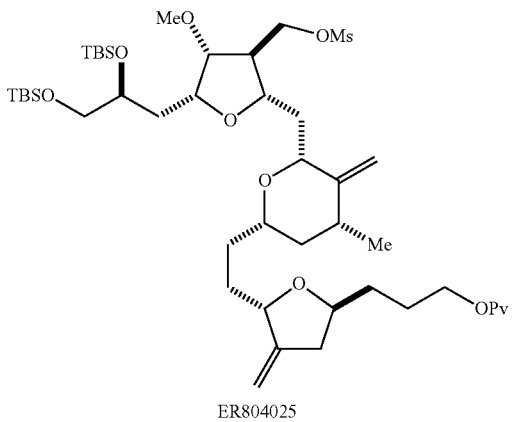

ER804025

To a solution of the alcohol, prepared as described in U.S. Pat. No. 6,214,865, 2.4 g, in methylene chloride, 29 mL, was added methanesulfonyl anhydride, 770 mg. The mixture was stirred for 15 minutes, extracted with saturated sodium bicarbonate, dried and chromatographed to give 2.737 g, 100%.

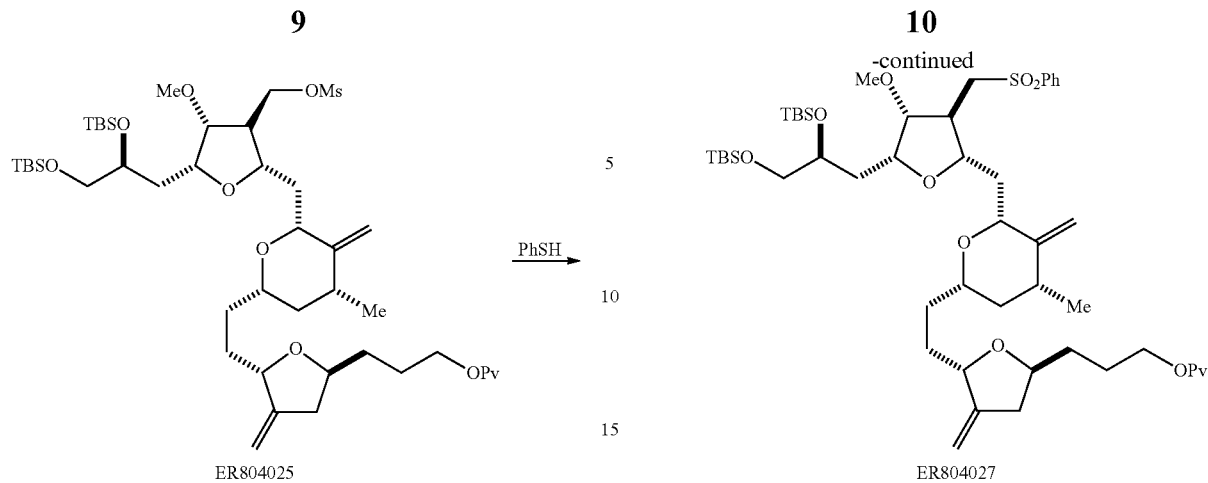

ER804025

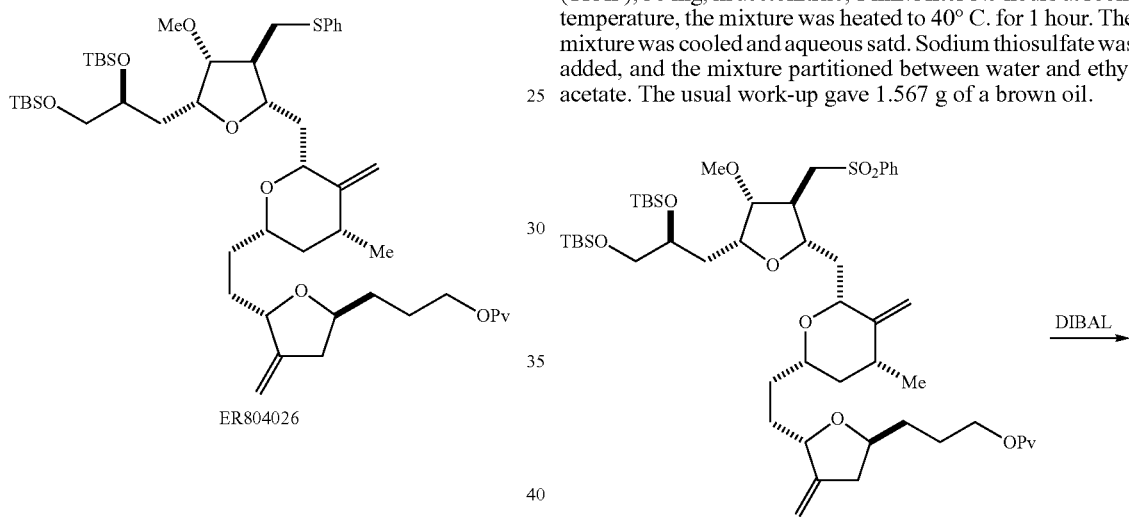

ER804026

To a solution of the mesylate, 405 mg, in DMF, 0.06 mL, was added di-isopropylethylamine, 0.130 mL, followed by benzenethiol, 0.061 mL. After 4 hours and after 22 hours, additional amine, 0.03 mL, and benzenethiol, 0.015 mL, were added. After 24 hours, the mixture was diluted with 5% ethyl acetate/hexane, 1 mL and chromatographed to give 409 mg.

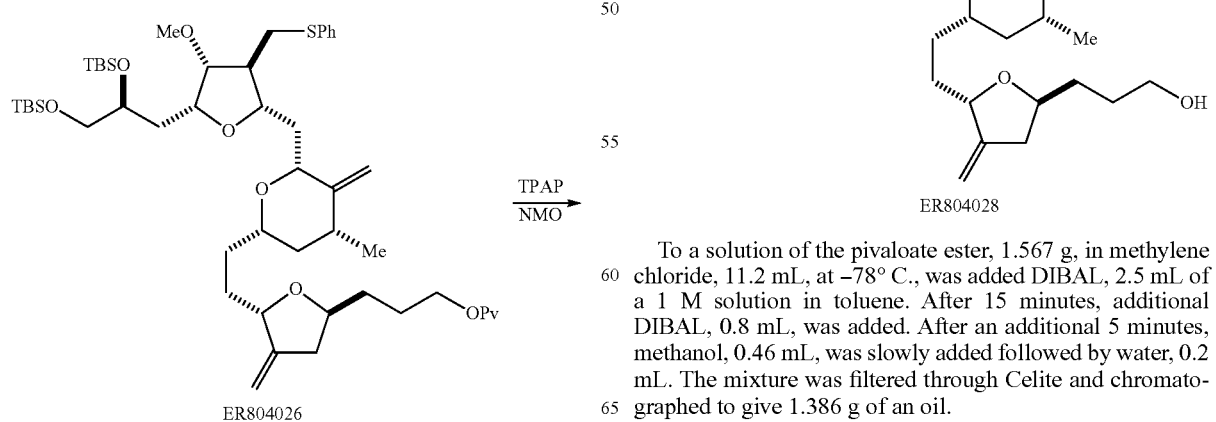

ER804026

ER804027

To a solution of the sulfide, 1.97 g, in acetonitrile, 16 mL, was added N-methylmorpholine oxide (NMO), and then a solution of 1.02 g, tetrapropylammonium perruthenate(VII), (TPAP), 38 mg, in acetonitrile, 1 mL. After 3.5 hours at room temperature, the mixture was heated to 40° C. for 1 hour. The mixture was cooled and aqueous satd. Sodium thiosulfate was added, and the mixture partitioned between water and ethyl acetate. The usual work-up gave 1.567 g of a brown oil.

ER804027

ER804028

To a solution of the pivaloate ester, 1.567 g, in methylene chloride, 11.2 mL, at −78° C., was added DIBAL, 2.5 mL of a 1 M solution in toluene. After 15 minutes, additional DIBAL, 0.8 mL, was added. After an additional 5 minutes, methanol, 0.46 mL, was slowly added followed by water, 0.2 mL. The mixture was filtered through Celite and chromatographed to give 1.386 g of an oil.

Key fragment F-3 can be obtained by DIBALH reduction of the corresponding methyl ester, XF3, as described above.

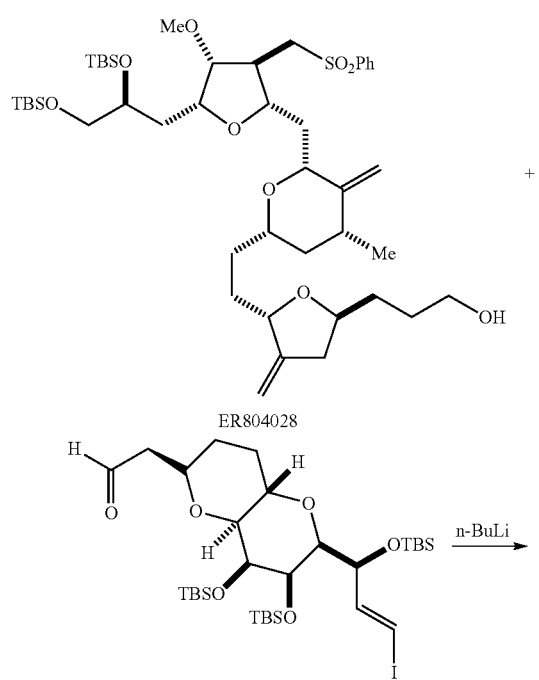

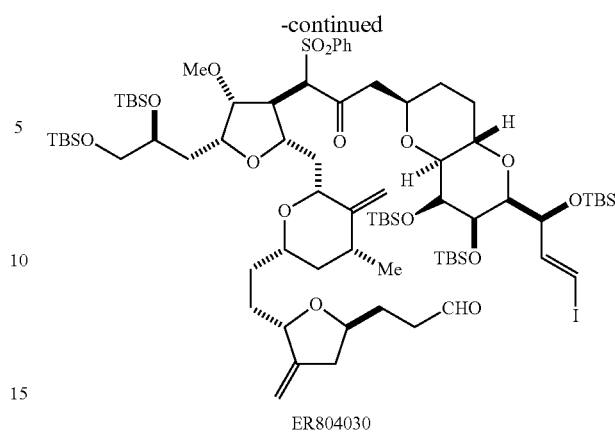

To a solution of the alcohol, 42 mg, in methylene chloride, 2 mL, was added the Dess Martin reagent, 36.4 mg. The mixture was stirred for 30 minutes, and ether was added. The mixture was filtered through Celite, washed with saturated sodium bicarbonate, with saturated sodium thiosulfate, worked up in the usual way, and chromatographed to give 38 mg of an oil.

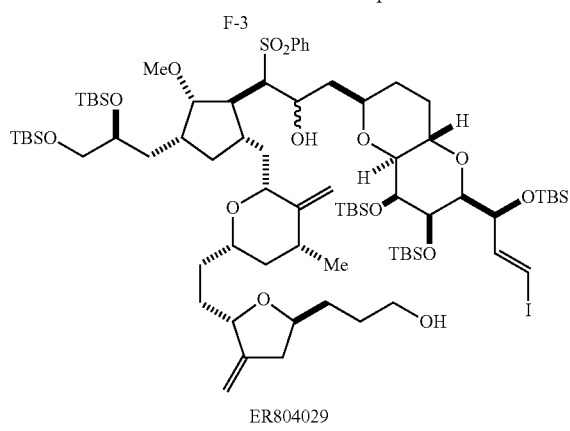

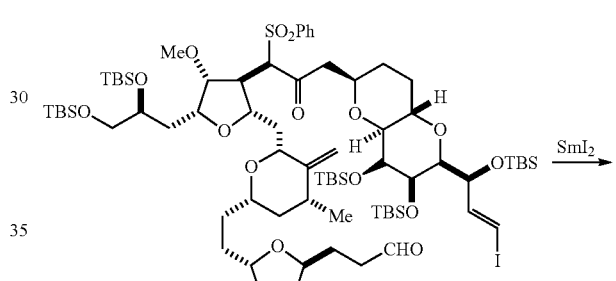

To a solution of the sulfone, 36 mg, in DME, 1 mL, at −40° C. was added n-butyllithium, 2.8 equivalents. After 35 minutes, a solution of the aldehyde, 42 mg, in DME, 0.5 mL, was added. After 40 minutes, saturated aqueous ammonium chloride was added, and the mixture extracted with ethyl acetate. The usual work-up, followed by chromatography gave 52 mg of an oil.

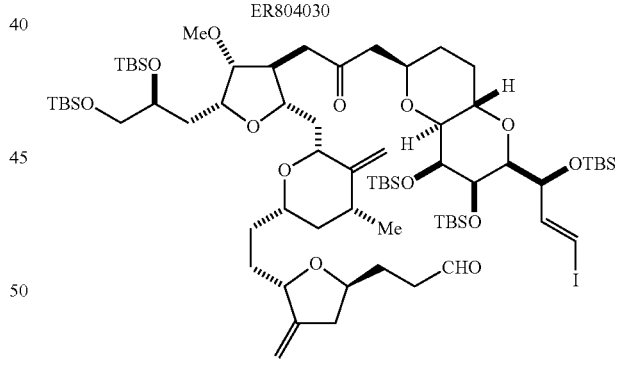

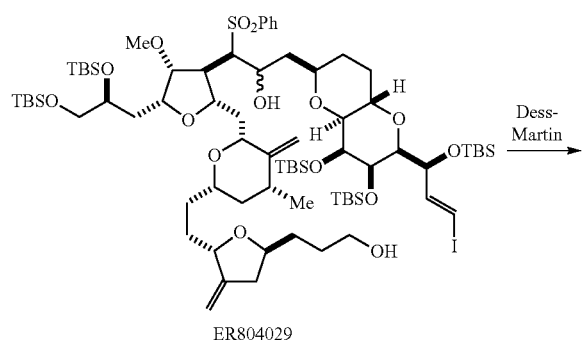

Preparation of $SmI_2$ Solution

A solution of 1,2-di-iodoethane in 10 mL of THF was added to a suspension of Sm, 0.16 g, in THF, 1 mL. The mixture was stirred for 1 hour.

An aliquot of this solution, 0.03 mL, was added to a solution of the sulfone in THF at −78° C. After 5 minutes, additional $SmI_2$ reagent, 0.05 mL, was added. After a few additional minutes, more reagent, 0.25 mL, was added. The cooling bath was removed, and saturated aqueous sodium bicarbonate, 3 mL, was added. The mixture was partitioned between ether and water, and the usual work-up gave 9.1 mg, 81%, of an oil.

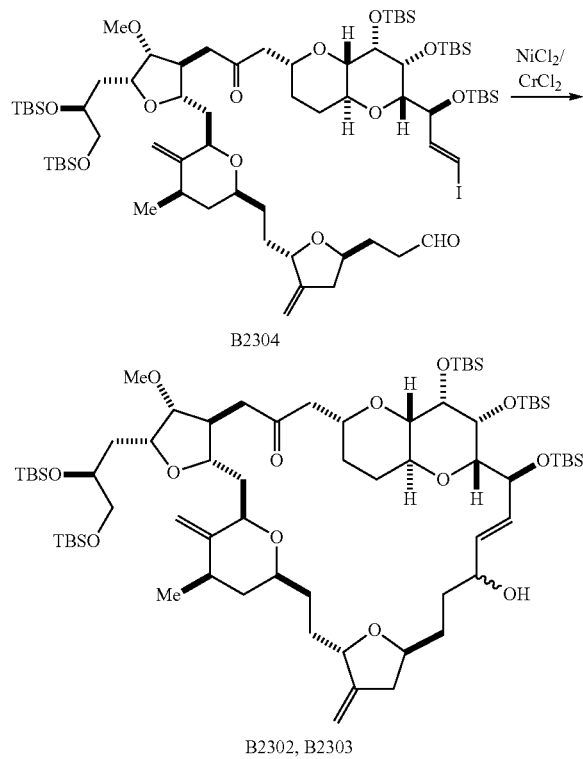
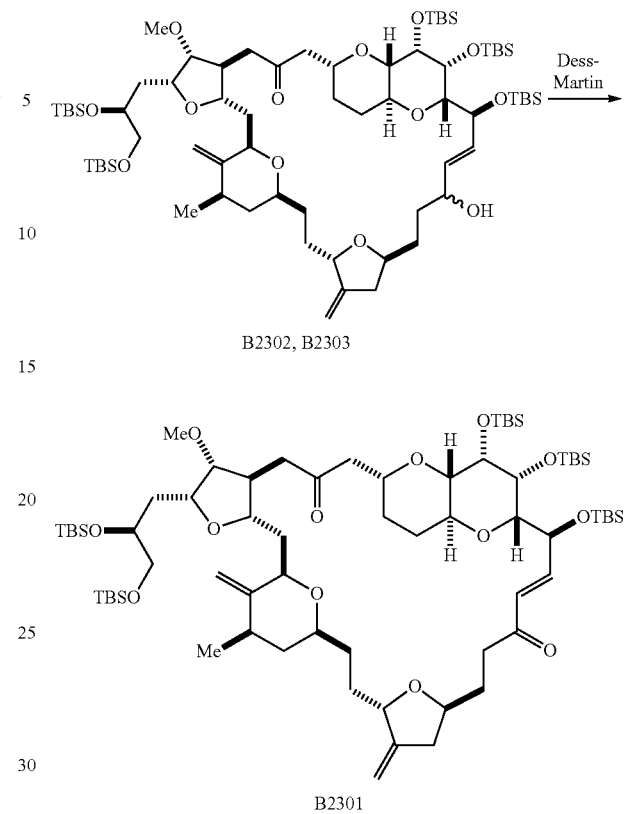

B2302 and B2303. In a glove box, NiCl₂/CrCl₂ (1% w/w, 1.09 g, 8.86 mmol) was added to a solution of B2304 (1.01 g, 0.70 mmol) in THF (600 mL) and DMF (150 mL) at rt. After stirring for 2 days the reaction mixture was taken out of the glove box, cooled to 0° C., quenched with saturated aqueous NH₄Cl (300 mL), and stirred at 0° C. for 20 min. After addition of H₂O (100 mL), the two layers were separated, and the aqueous layer was extracted with EtOAc (5×). The combined organic phases were washed with brine, dried over Na₂SO₄, concentrated, and purified by column chromatography (15% EtOAc-hexanes) to furnish a mixture of B2302 and B2303 (0.84 g, 92%) as a solid foam. Although the isomers could be separated by prep TLC (20% EtOAc-hexanes), they were carried forward as a mixture.

B2301. A mixture of B2302/B2303 (0.79 g, 0.60 mmol) and Dess-Martin periodinane (0.26 g, 0.60 mmol) in CH₂Cl₂ (30 mL) at rt was stirred for 30 min. Additional Dess-Martin periodinane (0.26 g, 0.60 mmol) was added to the mixture, and stirring was continued for an additional 1.5 h. The mixture was then diluted with Et₂O (100 mL), stirred for 15 min, and filtered through Celite. The filtrate was washed with saturated aqueous NaHCO₃ (100 mL), and the separated aqueous layer was extracted with Et₂O (3×). The combined organic phases were dried over Na₂SO₄, concentrated, and purified by column chromatography (10% to 15% EtOAc-hexanes) to give B2301 (0.67 g, 85%) as an oil.

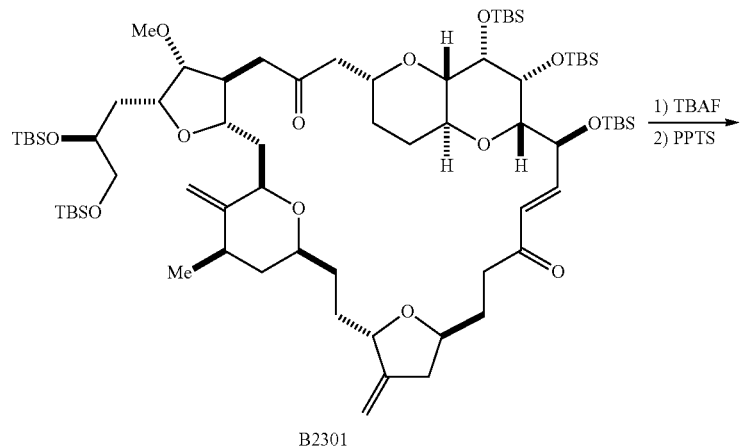

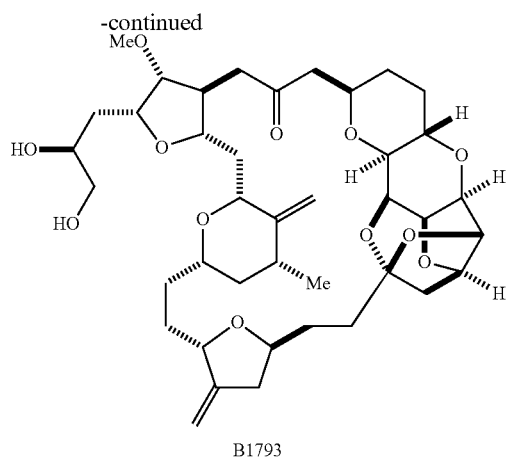

B1793

B1793. TBAF (1 M in THF containing 0.5 M imidazole HCl, 4.60 mL, 4.60 mmol) was added over 2 min to a solution of B2301 (0.62 g, 0.48 mmol) in THF (29 mL) at rt, and the resulting mixture was stirred for 18 h. After dilution with hexanes (10 mL), the reaction mixture was directly loaded onto a $SiO_2$ column packed with 50% EtOAc-hexanes and eluted with 50% EtOAc-hexanes (1 L) followed by 10% MeOH/EtOAc to collect a mixture of intermediates. After solvent removal, the residue was dissolved in $CH_2Cl_2$ (15 mL) and treated with PPTS (645 mg). After stirring for 1 h at rt, additional PPTS (414 mg) was added, and the resulting white suspension was stirred for 4.5 h. The reaction mixture was then directly loaded onto a $SiO_2$ column packed with 70% EtOAc-hexanes and eluted with 70% EtOAc/hexanes (0.5 L), EtOAc (1 L). Elution with 5% to 10% MeOH/EtOAc furnished pure B1793 (181 mg) and elution with 15% MeOH-EtOAc gave additional semi-pure product, which after purification by preparative TLC (10% MeOH-EtOAc) provided additional pure B1793 (42 mg). B1793 (total 223 mg, 64%) was obtained as a white solid. HRMS: calcd for $C_{40}H_{58}O_{12}$+ Na 753.3826. Found: 753.3808.

The invention provides methods for treating cancer, involving administration of a halichondrin B analog, such as an analog having the following structure:

B1939

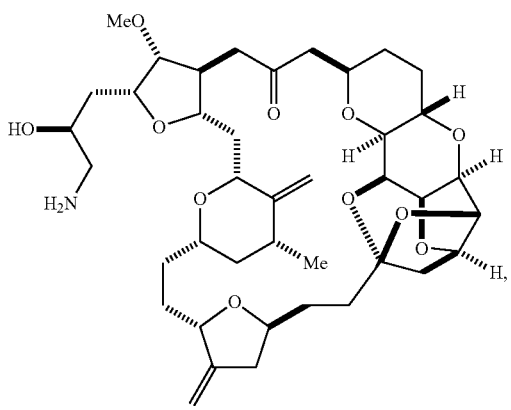

which is carried out in combination with a second approach to treatment.

There are numerous types of anti-cancer approaches that can be used in conjunction with halichondrin B analog treatment, according to the invention. These include, for example, treatment with chemotherapeutic agents (see below), biological agents (e.g., hormonal agents, cytokines (e.g., interleukins, interferons, granulocyte colony stimulating factor (G-CSF), macrophage colony stimulating factor (M-CSF), and granulocyte macrophage colony stimulating factor (GM-CSF)), chemokines, vaccine antigens, and antibodies), anti-angiogenic agents (e.g., angiostatin and endostatin), radiation, and surgery.

The methods of the invention can employ these approaches to treat the same types of cancers as those for which they are known in the art to be used, as well as others, as can be determined by those of skill in this art. Also, these approaches can be carried out according to parameters (e.g., regimens and doses) that are similar to those that are known in the art for their use. However, as is understood in the art, it may be desirable to adjust some of these parameters, due to the additional use of a halichondrin B analog with these approaches. For example, if a drug is normally administered as a sole therapeutic agent, when combined with a halichondrin B analog, according to the invention, it may be desirable to decrease the dosage of the drug, as can be determined by those of skill in this art. Examples of the methods of the invention, as well as compositions that can be used in these methods, are provided below.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with halichondrin B treatment, according to the invention. Specific, non-limiting examples of these classes of drugs, as well as cancers that can be treated by their use, are as follows.

Antimetabolite drugs that halichondrin B analogs can be used with include, e.g., methotrexate, purine antagonists (e.g., mercaptopurine, thioguanine, fludarabine phosphate, cladribine, and pentostatin), and pyrimidine antagonists (e.g., gemcitabine, capecitabine, fluorouracil (e.g., 5-FU), cytarabine, and azacitidine). Use of these agents to treat particular types of cancers is well known in the art, and these agents can be used in combination with halichondrin B analogs to treat these and other types of cancers. As specific, non-limiting examples, a halichondrin B analog can be used with gemcitabine in the treatment of non-small cell lung carcinoma, pancreatic cancer, or metastatic breast cancer. In an additional example, a halichondrin B analog can be used in conjunction with capecitabine in the treatment of breast or colorectal cancers.

As is noted above, another class of chemotherapeutic drugs with which halichondrin B analogs can be used includes anticancer antibiotics. These include, for example, anthracyclines (e.g., doxorubicin, epirubicin, daunorubicin, and idarubicin), adriamycin, dactinomycin, idarubincin, plicamycin, mitomycin, and bleomycin. As with the drugs mentioned above, use of these agents to treat particular types of cancers is well known in the art, and they can be used in combination with halichondrin B analog treatment to treat these and other types of cancers. As a specific, non-limiting example, an anthracycline, such as doxorubicin, can be administered in conjunction with halichondrin B therapy for the treatment of breast or pancreatic cancers. Alternatively, a third agent, cyclophosphamide, can be used in this method.

Alkylating agents comprise another class of chemotherapeutic drugs that can be administered in conjunction with a halichondrin B analog, according to the invention. Examples of such drugs include procarbazine, dacarbazine, altretamine, cisplatin, carboplatin, and nitrosoureas. Halichondrin B analogs can be used with these agents in the treatment of cancers that these agents are known in the art to be used to treat, as well as in the treatment of other cancers. For example, a halichondrin B analog can be used in conjunction with carboplatinum in the treatment of non-small cell lung carcinoma or ovarian cancer.

An additional type of chemotherapeutic drug with which halichondrin B analogs can be administered, according to the invention, is plant alkaloids, such as vinblastine, vincristine, etoposide, teniposide, topotecan, irinotecan, paclitaxel, and docetaxel. As specific, non-limiting examples, a halichondrin B analog can be used in conjunction with irinotecan for the treatment of colorectal cancer, or with topotecan in the treatment of ovarian or non-small cell lung cancers.

Further types of anti-cancer agents that can be used in conjunction with halichondrin B analog treatment, according to the invention, are anticoagulants and antithrombotic agents. For example, heparin (e.g., low molecular weight heparin or heparin sulfate) or warfarin can be used. Use of these agents in treating patients by, for example, injection or oral administration, is well known in the art, and thus they can readily be adapted by those of skill in the art for use in the present invention.

Numerous approaches for administering anti-cancer drugs are known in the art, and can readily be adapted for use in the present invention. In the case of one or more drugs that are to be administered in conjunction with a halichondrin B analog, for example, the drugs can be administered together, in a single composition, or separately, as part of a comprehensive treatment regimen. For systemic administration, the drugs can be administered by, for example, intravenous infusion (continuous or bolus). Appropriate scheduling and dosing of such administration can readily be determined by those of skill in this art based on, for example, preclinical studies in animals and clinical studies (e.g., phase I studies) in humans. In addition, analysis of treatment using similar drugs, as well as monitoring factors such as blood counts (e.g., neutrophil and platelet counts) and vital signs in patients can be used, as is well understood in the art.

Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment. It may be desirable to use both drugs at each administration or, alternatively, to have some (or all) of the treatments include only one drug (or a subset of drugs).

As a specific, non-limiting example of a treatment regimen included in the invention, a halichondrin B analog (e.g., 0.01-5 mg/m$^2$) can be administered to a patient by intravenous infusion for 0.5-3 hours, followed by intravenous infusion of another drug (e.g., gemcitabine, e.g., 500-900 mg/m$^2$) for 0.5-3 hours. This course of treatment can be repeated every 2-3 weeks, as determined to be tolerable and effective by those of skill in the art. In a variation of this method, the treatment is carried out with both drugs on the first day, as is noted above, but then is followed up with treatment using only the secondary drug (e.g., gemcitabine) in ensuing weeks.

Further, as is well known in the art, treatment using the methods of the invention can be carried out in conjunction with the administration of antiemetics, which are drugs that are used to reduce the nausea and vomiting that are common side effects of cancer chemotherapy. Examples of such drugs include major tranquilizers (e.g., phenothiazines, such as chlorpromazine and prochlorperazine), dopamine antagonists (e.g., metoclopramide), serotonin antagonists (e.g., ondansetron and granisetron), cannabinoids (e.g., dronabinol), and benzodiazepine sedatives.

In addition to the cancers mentioned above, the methods and compositions of the invention can be used to treat the following types of cancers, as well as others: skin (e.g., squamous cell carcinoma, basal cell carcinoma, or melanoma), prostate, brain and nervous system, head and neck, testicular, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) cancers. Other types of cancers that can be treated using the methods of the invention include fibrosarcoma, neurectodermal tumor, mesothelioma, epidermoid carcinoma, and Kaposi's sarcoma.

The invention also includes compositions that include a halichondrin B analog in combination with an additional therapeutic agent(s), such as any of those agents listed above. The drugs in these compositions preferably are formulated for administration to patients (e.g., in physiological saline) or, alternatively, can be in a form requiring further processing prior to administration. For example, the compositions can include the drugs in a lyophilized form or in a concentrated form requiring dilution. Formulation of drugs for use in chemotherapeutic methods can be carried out using standard methods in the art (see, e.g., *Remington's Pharmaceutical Sciences* (18$^{th}$ edition), ed. A. Gennaro, 1990, Mack Publishing Co., Easton, Pa.).

What is claimed is:
1. A compound having the formula:

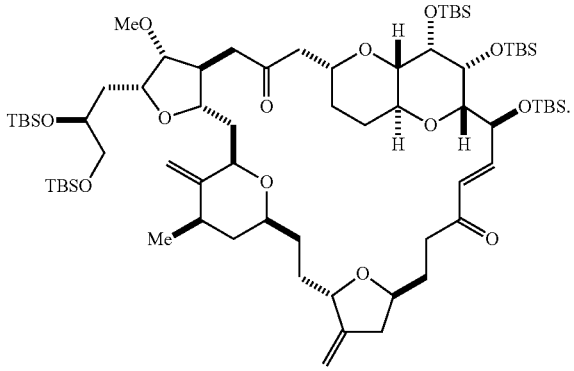

2. A compound having the formula:
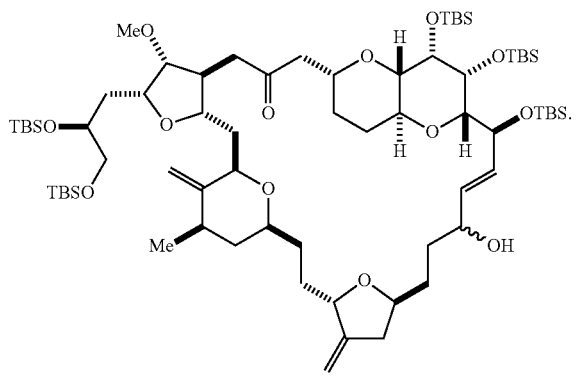
3. A compound having the formula:
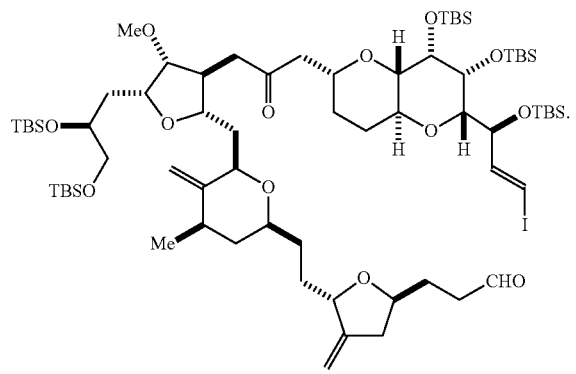
4. A compound having the formula:
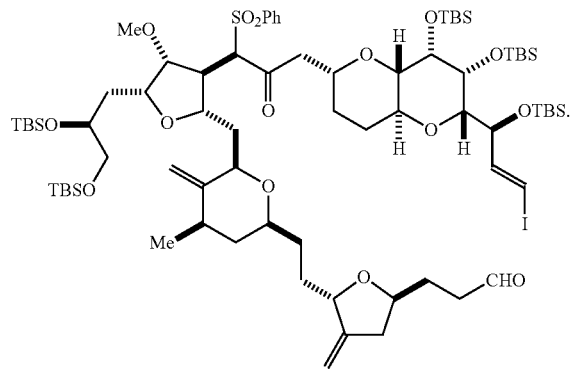
5. A compound having the formula:
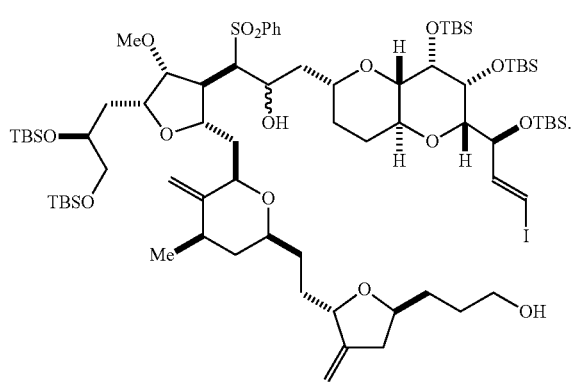
6. A method of preparing:
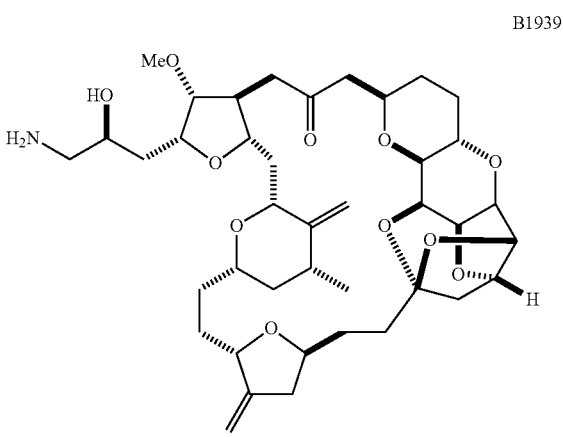
or a pharmaceutically acceptable salt thereof, the method comprising the steps of
synthesizing a compound selected from the group consisting of
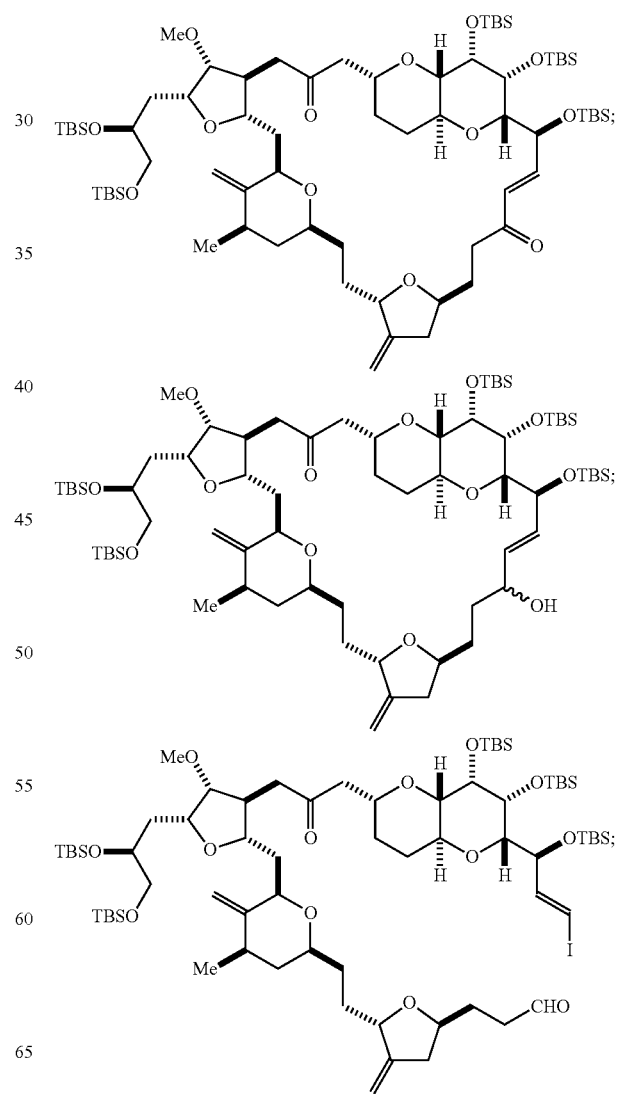

-continued
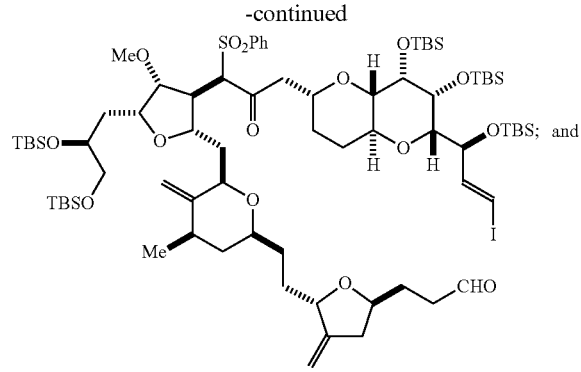
and
synthesizing B1939 or the pharmaceutically acceptable salt from the compound.
7. A method of preparing:
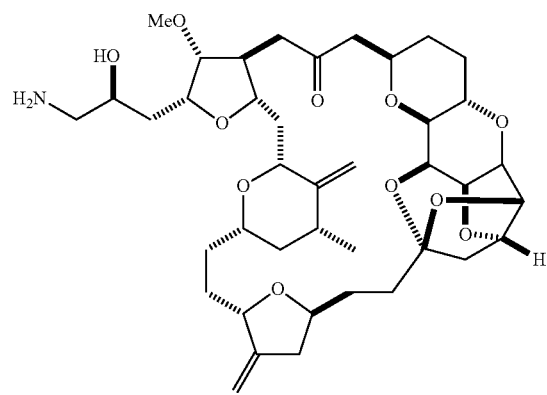
B1939
or a pharmaceutically acceptable salt thereof, the method comprising the steps of reacting
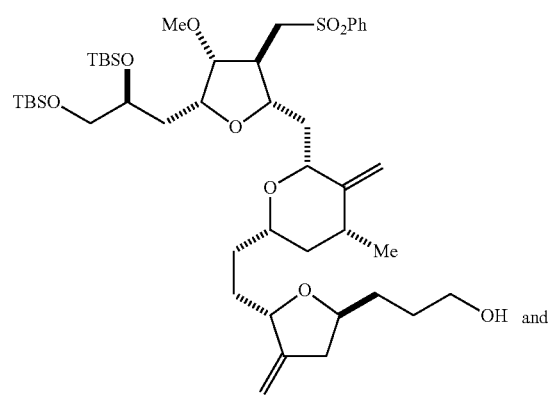
ER804028
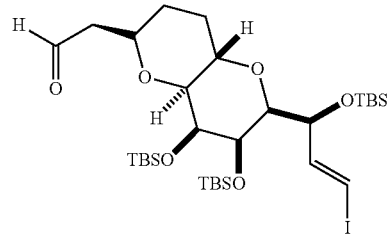
F-3
under conditions to produce:
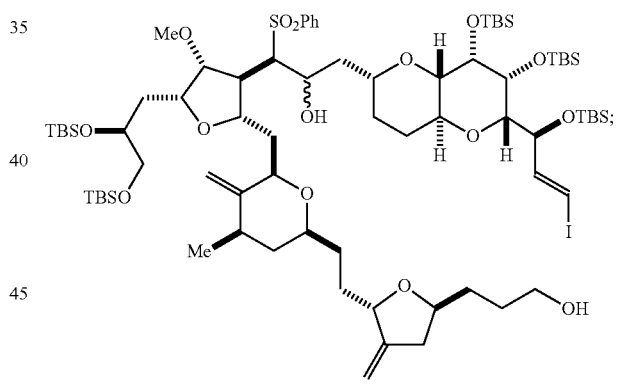
ER804029
reacting ER804029 under conditions to produce:
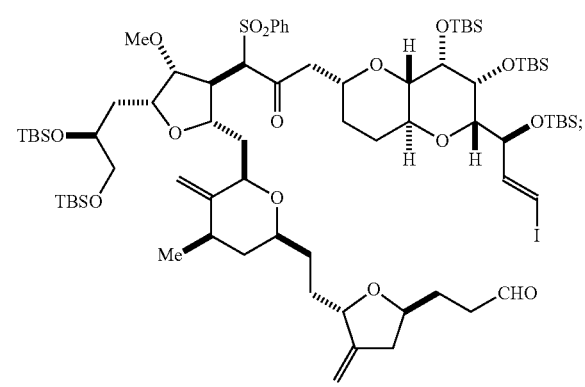
ER804030 reacting ER804030 under conditions to produce:
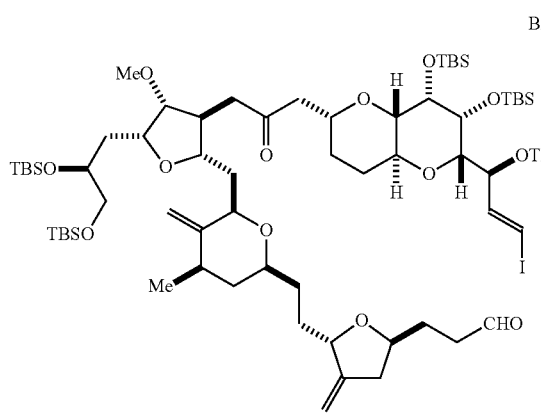
reacting B2304 under conditions to produce:
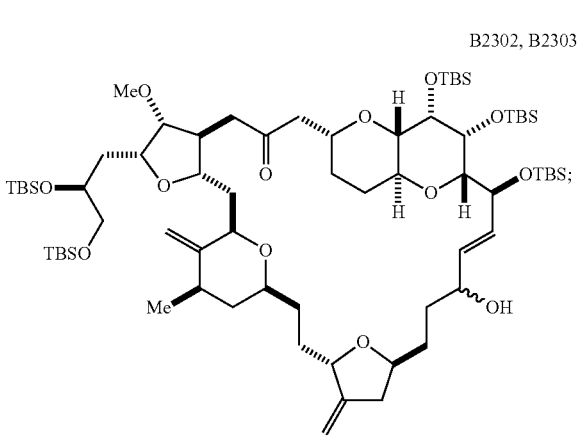
reacting B2303, B2303 under conditions to produce:
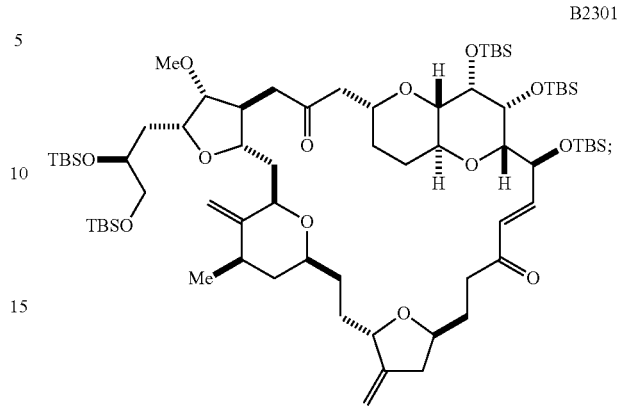
reacting B2301 under conditions to produce:
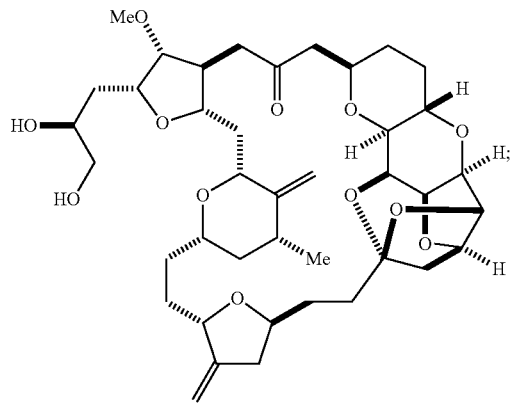
and
reacting B1793 under conditions to produce B1939 or the pharmaceutically acceptable salt.
* * * * *

UNITED STATES PATENT AND TRADEMARK OFFICE
CERTIFICATE OF CORRECTION

PATENT NO.        : 8,148,554 B2
APPLICATION NO.   : 12/855412
DATED             : April 3, 2012
INVENTOR(S)       : Boris M. Seletsky et al.

Page 1 of 1

It is certified that error appears in the above-identified patent and that said Letters Patent is hereby corrected as shown below:

In the Claims

Column 24, Line 1, replace "reacting B2303, B2303" with --reacting B2302, B2303--

Signed and Sealed this
Fifth Day of May, 2015

Michelle K. Lee
*Director of the United States Patent and Trademark Office*